(12) United States Patent
Dvorak et al.

(10) Patent No.: US 8,972,272 B1
(45) Date of Patent: Mar. 3, 2015

(54) WORKSTATION WITH BEDSIDE PORTAL

(75) Inventors: Carl D. Dvorak, Verona, WI (US); Stirling B. Martin, Madison, WI (US); Aaron M. Webb, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 508 days.

(21) Appl. No.: 12/882,721

(22) Filed: Sep. 15, 2010

Related U.S. Application Data (60) Provisional application No. 61/243,416, filed on Sep. 17, 2009.

(51) Int. Cl.
*G06F 19/00* (2011.01)

(52) U.S. Cl.
USPC .......................................................... 705/3

(58) Field of Classification Search
USPC ........ 705/3; 600/301, 365; 340/5.8; 345/130, 345/173; 128/668
See application file for complete search history.

(56) References Cited

U.S. PATENT DOCUMENTS

| | | | |
|---|---|---|---|
| 5,706,822 A * | 1/1998 | Khavari | 600/483 |
| 6,002,427 A | 12/1999 | Kipust | |
| 6,047,259 A | 4/2000 | Campbell et al. | |
| 6,211,856 B1 * | 4/2001 | Choi et al. | 345/666 |
| 6,300,943 B1 * | 10/2001 | Shmunis | 345/173 |
| 6,570,610 B1 | 5/2003 | Kipust | |
| 7,949,547 B2 | 5/2011 | Matz | |
| 2005/0076060 A1 | 4/2005 | Finn et al. | |
| 2006/0080140 A1 | 4/2006 | Buttner et al. | |
| 2008/0106374 A1 * | 5/2008 | Sharbaugh | 340/5.8 |
| 2008/0249386 A1 * | 10/2008 | Besterman et al. | 600/365 |
| 2008/0316045 A1 | 12/2008 | Sriharto et al. | |
| 2010/0249540 A1 * | 9/2010 | Lisogurski | 600/301 |

\* cited by examiner

*Primary Examiner* — John Pauls
(74) *Attorney, Agent, or Firm* — Boyle Fredrickson, S.C.

(57) ABSTRACT

A room-based terminal near the patient's bedside is used to supplement the operation of a patient care computing device to improve contemporaneous data capture and information accessibility during a healthcare provider's rounds. The particular benefits of the stationary terminal and patient care computing device augment each other in providing superior workflow.

19 Claims, 10 Drawing Sheets

WORKSTATION WITH BEDSIDE PORTAL

CROSS REFERENCE TO RELATED APPLICATION

This application claims the benefit of U.S. Provisional Application No. 61/243,416, filed Sep. 17, 2009, hereby incorporated by reference in its entirety.

STATEMENT REGARDING FEDERALLY SPONSORED RESEARCH OR DEVELOPMENT

BACKGROUND OF THE INVENTION

The present invention relates generally to workstations used by hospital staff in attending to patients and, in particular, to an electronic medical record system working with such workstations.

The transition from paper records to electronic medical records in the hospital environment has been facilitated by the use of patient care computing devices. For example, mobile computing devices are transported from patient room to patient room by a healthcare provider and can include laptop computers, tablet computers, etc. One exemplary mobile computing device is known, as "computers on wheels" (COWs) or more commonly as "workstations on wheels" (WOWs). Alternatively, many patient rooms are provided with the same functionality in a fixed workstation in each patient's room.

A WOW provides a mobile computer workstation, typically communicating with a centralized database via wireless link, combined with a supply cart holding medical supplies and the like. The WOW permits a healthcare provider attending patients to electronically capture medical data related to the patient. The data may be entered, for example, through a keyboard and mouse or similar cursor control device on the workstation or by using devices such as a barcode scanner capturing data from medicine containers and the like, as medicine is administered, to record and verify proper dosages.

Similarly, a mobile or fixed workstation may be used by the healthcare provider to allow direct entry of data while in the patient's room. The entered data may be received from one or more medical monitoring devices, the result of patient observation, the result of patient interaction, etc.

In some situations, particularly in the intensive care unit (ICU) where ready access to the patient's bedside by a cart is blocked by equipment, the effectiveness of the WOW or other computing device is significantly decreased. In such cases, the healthcare provider must park the WOW away from the patient, for example in an adjoining hall, preventing contemporaneous interaction with the WOW in providing data to the healthcare provider and recording observations. Where a fixed or mobile computing device is used, the healthcare provider may not be able to position the device proximate to the patient such that the caregiver can both interact with the patient and enter data and receive information using the computing device.

SUMMARY OF THE INVENTION

The present inventors have recognized that the utility of patient care computing devices during patient interaction can be greatly enhanced by the use of a limited function bedside terminal synchronized with the patient care computing device. By duplicating a subset of the data communicated to and from the patient care computing device with the bedside terminal, seamless electronic record keeping and communication can be obtained practically with current technology.

Specifically, the present invention provides an electronic medical record system having a medical database system, a patient care computing device, and at least one stationary, room-based terminal. The medical database system provides a communication interface for receiving and transmitting medical data related to patients. The patient care computing devices, in turn, provides a computing device including an electronic display, a text entry device, and a network circuit communicating with the medical database system. In one embodiment, the computing device is provided on a mobile cart providing carrier surfaces for medical supplies and for the patient care computing device. Finally, the stationary, room-based terminals provide an electronic display adapted for mounting relative to a bedside associated with a given patient and a network circuit communicating with the medical database system. The medical database system, patient care computing device, and room-based terminal execute at least one stored program to: (a) manage a secure log-on by a health care worker to the patient care computing device; (b) receive through the patient care computing device after log-on an identification of a patient; (c) communicate patient medical data related to the patient from the medical database to the patient care computing device; and (d) provide duplicate communication of at least a portion of the patient medical data from the medical database to a room-based terminal associated with a bedside of the patient.

It is thus one feature of at least one embodiment of the invention to combine the advantageous features of both a patient care computing device and stationary terminal in managing patient care. The combination, for example, can take advantage of the large format display possible with a stationary terminal and the improved privacy, security, and data entry capabilities of the patient care computing device.

The stored program may include a patient-room lookup table mapping a patient to an address of a room-based terminal associated with a bedside of the patient, wherein the medical database system further includes a means for directing the duplicate communication according to the address.

It is thus one feature of at least one embodiment of the invention to permit the room-based terminals to be blanked or used for other purposes when not being enlisted to supplement the functionality of the patient care computing device and to be activated selectively (either manually or automatically) upon access to the patient's records.

The room-based terminal and patient care computing device may provide for input of medical data and the stored program may further communicate medical data from the room-based terminal and patient care computing device to the medical database records related to the patient.

It is thus one feature of at least one embodiment of the invention to permit contemporaneous recording of medical data when the patient care computing device cannot be brought into proximity to the patient. The entry of data via the room-based terminal avoids the need for the healthcare provider to accurately remember medical data or resort to informal recording of such data on slips of paper or the like such as may lead to data loss or mis-transcription The medical data from the room-based terminal may be presented at the patient care computing device for verification before being accepted into the medical database records of the patient.

It is thus one feature of at least one embodiment of the invention to eliminate the need for the healthcare provider to execute multiple user security protocols with each of the room-based terminals and to reduce security problems in this environment.

The medical data from the room-based terminal may alternatively or in addition be presented at the patient care computing device for supplementation before being accepted in the medical database records of the patient.

It is thus one feature of at least one embodiment of the invention to accommodate limited data entry capabilities of a room-based terminal by permitting that data to be augmented or annotated using a full-featured computing device such as the patient care computing device.

The stored program may provide a message prioritization for at least some medical data input at the patient care computing device to be communicated to the room-based terminal on an expedited basis with respect to other messages communicated among the patient care computing device, room-based terminal, and medical database system based on medical significance of data of the message.

It is thus one feature of at least one embodiment of the invention to ensure uninterrupted communication from practice tools, such as automatic patient monitoring devices, implemented by the patient care computing device and medical database system to the healthcare provider during the healthcare provider's rounds when data may be displayed on separate augmenting terminals.

The electronic medical record system may further include a device for recording the administration of medicine; the device in communication with the patient care computing device and the stored program may provide an advisory based on recordation of medicine administration at both the patient care computing device and the room-based terminal.

It is thus one feature of at least one embodiment of the invention to ensure timely advisories to the healthcare provider related to the administration of medicine when data entry and/or data display are separated between a patient care computing device and room-based display.

The room-based terminal may be a touch screen.

It is thus one feature of at least one embodiment of the invention to provide a data entry mechanism for the room-based terminal compatible with wall mounting of the in-room terminal or the like.

The room-based terminal may provide graphical elements for quantitative data entry employing a detection of a sliding of a stylus on the touch screen.

It is thus one feature of at least one embodiment of the invention to permit rapid and convenient quantitative data entry using a touch screen system.

The room-based terminal provides a plurality of display icons that may be touched to expand them to larger icons. The display icons may be icons, graphed representations of data, etc.

It is thus one feature of at least one embodiment of the invention to provide comprehensive data overview possible in a large format display, while permitting an arbitrary level of detail on a selective basis, to be compatible with a role in augmenting a patient care computing device.

The electronic medical system may receive data identifying an imputed observer of the room-based terminal and the duplicate communication may be selectively displayed according to the identification of the imputed observer.

It is thus one feature of at least one embodiment of the invention to reduce the possibility of revealing sensitive patient information to non-authorized individuals as might otherwise present a problem with a room-based terminal.

The identification of an imputed observer may be performed by a presence sensing of at least one person in proximity to the room-based terminal.

It is thus one feature of at least one embodiment of the invention to provide automatic switching of display modes in the room-based terminals to reduce the possibility of revealing sensitive information, while reducing interference with the healthcare provider's normal workflow.

The stored program may provide a set of priority rules identifying one imputed observer when there are multiple persons sensed in proximity to the room-based terminal.

It is thus one feature of at least one embodiment of the invention to permit the display to be properly tailored to the viewers when multiple viewers are present.

The identification of an imputed observer may be performed by detecting a current identification of the patient record selected at one or more patient care computing devices associated with the room-based terminal.

It is thus one feature of at least one embodiment of the invention to provide mode changes to the room-based display that are triggered automatically by the normal process of the healthcare provider calling up the records of the patient at the patient care computing device.

The stored program may further operate to display supplementary information on the room-based terminal related to generic roles of imputed observers selected from at least two of the group consisting of a physician imputed user, a family member imputed user, a case manager imputed user and a nurse imputed user.

It is thus one feature of at least one embodiment of the invention to provide for alternative uses of the room-based display when not being used by the healthcare provider, allowing more cost-effective implementation that promotes adoption of this system.

These particular objects and advantages may apply to only some embodiments falling within the claims and thus do not define the scope of the invention.

DETAILED DESCRIPTION OF THE PREFERRED EMBODIMENT

Figure 1:
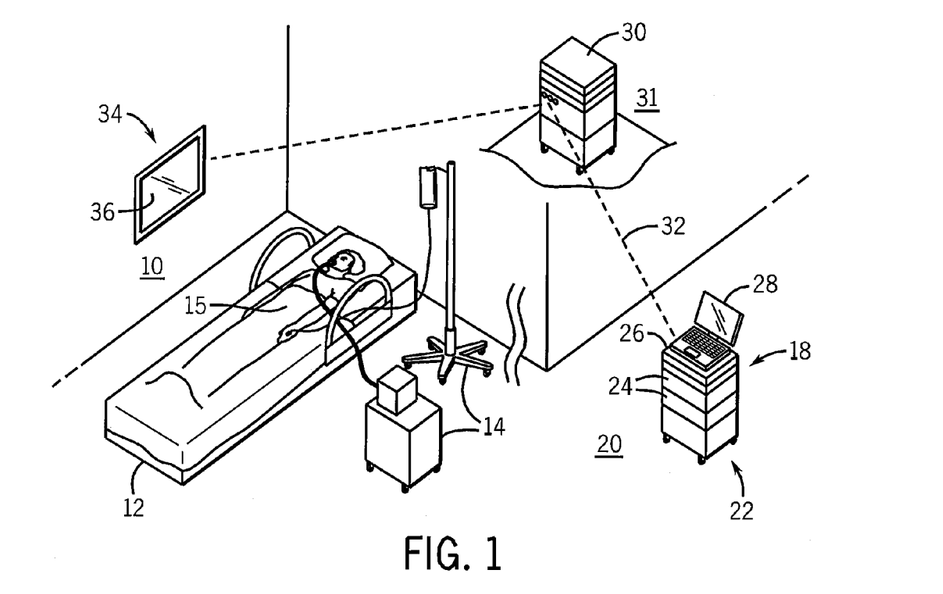
FIG. 1 is a simplified perspective view of an intensive care unit showing principal components of the present invention including a patient care computing device, a room-based terminal, and a medical database system in communication with the workstation on wheels.

Referring now to FIG. 1, a patient room 10 may provide for a patient bed 12 associated with a patient 15 under care. The patient room 10 may include a standard hospital room or rooms used for intensive care. Particularly in the latter situation, the patient bed 12 may be obstructed entirely or partially by medical equipment 14 whose movement may be further limited by various connections to the patient 15 and the equipment 14. In such cases, a mobile work unit 18 used by a healthcare provider (not shown) in attending to the patient 15 may be parked in a location remote from the patient bed 12 while the healthcare provider attends to the patient 15.

As is generally understood in the art, the mobile work unit 18 may be a workstation on wheels (WOW) or similar product providing a wheeled cart 22 with drawers or shelves 24 holding medical supplies and a support surface 26 holding a portable patient care computing device 28 such as a laptop computer. The wheeled cart 22 may also support a battery for the patient care computing device 28.

The patient care computing device 28 will be in communication with a medical database system 30 typically located in an environmentally controlled room 31 removed from the patient room 10 and the hallway 20. The communication may be conducted by signals 32 passing wirelessly, for example, by radio link connected to the medical database system 30 possibly through repeaters and the like as is generally understood in the art.

Although shown in conjunction with a mobile work unit 18, the patient care computing device 28 may alternatively be a fixed computing device, a portable computing device such as a laptop computer, a tablet computer, a handheld computing device, etc. Even with such devices, the same problems faced while using the mobile work unit 18 are present. A fixed computing device will most likely be located in an area of the patient's room that is removed from the patient. Similarly, a healthcare provider may not be able to set up a portable computing device proximate to the patient because of a lack of available surfaces. Even where the patient care computing device, it is often the situation where a healthcare provider will not be able to both provide proper care and view and interact with the patient care computing device.

The present invention further provides at least one stationary room-based terminal 34, for example mounted on the wall of the patient room 10 or mounted on a pedestal or the like, intended to be associated with the patient 15 during the duration of the patient's care and thus to be practically stationary. The room-based terminal 34 provides a display area 36 visible to those attending to the patient and optionally visible to the patient and patient's family and provides for a network circuit for communication with the medical database system 30 either wirelessly or by wire connections or a combination of both. The room-based terminals 34 may optionally also communicate with the patient care computing device 28.

Generally, when the healthcare provider must park the wheeled cart 22 in the hallway 20 because of obstructions about the patient bed 12 or for other reasons, continuity of communication with the medical database system 30 is ensured by the coordinated actions of the patient care computing device 28 and room-based terminal 34 as will be described in greater detail below.

Hardware Description

Figure 2:
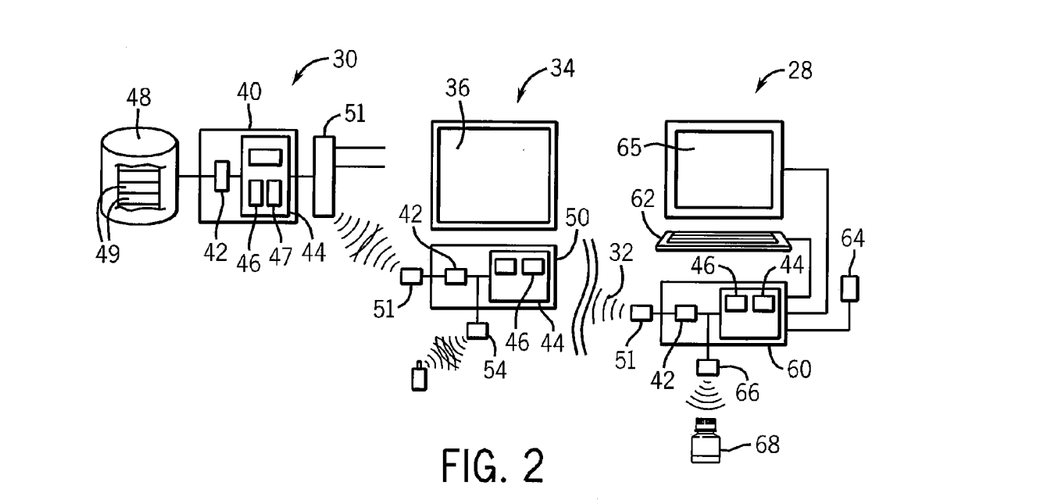
FIG. 2 is a functional block diagram showing functional elements of the principal components of the present invention.

Referring now to FIG. 2, the medical database system 30 will generally include a computer 40 having a processor 42 communicating with memory 44. The memory 44 may hold a standard operating system (not shown), and a medical database program 47, for example, of the type manufactured by Epic Systems Corporation of Verona, Wis. under the tradenames of EpicCare, Epicenter and operating in coordination with a program 46 of the present invention as will be described below. The computer 40 may communicate with mass storage device 48 containing medical records 49 identified to individual patients having multiple fields holding clinical medical data of a type collected by health care professionals in the course of their duties in caring for patients. The computer 40 may also connect with a network circuit 51 providing for wired or wireless communications with other devices as described above and generally understood in the art.

The room-based terminal 34 will generally include a computer 50 also providing a processor 42 and memory 44, the latter holding an operating system and the program 46 of the present invention in whole or in part. The computer 50 may provide display signals to a screen having a large display area 36 such as an LCD or plasma panel display having a touch surface providing input signals to the computer 50. Computer 50 may also communicate with a network circuit 51 providing for wired or wireless communication with the medical database system 30 and may include a proximity sensor 54 such as an RFID tag reader that may read RFID tags or the like worn by physicians or others to identify possible viewers of the display area 36. Location sensing and/or viewer identification may also be implemented using one or more alternative systems generally known in the art.

The patient care computing device 28 will generally include a computer 60 providing a processor 42 and a memory 44, the latter holding all or a portion of the program 46 of the present invention. A computer 60 may communicate with a keyboard 62 and a cursor control device 64 such as a touchpad and with a small format display 65 of the type normally associated with a laptop computer. The computer 60 may also have other data entry devices including, for example, a reader 66 such as a barcode reader for scanning medicines 68 immediately prior to their administration. The computer 60 also communicates with a network circuit 51 providing for wired or wireless communication with the medical database system 30 and possibly the room-based terminal 34.

The operation of these components of the patient care computing device 28, medical database system 30, and room-based terminal 34 is provided by stored software of program 46 executed by these devices. The functions of the program 46 may be flexibly distributed among the devices or substantially centralized in a given device, for example, the medical database system 30.

General Data Flow and Operation

Figure 3:
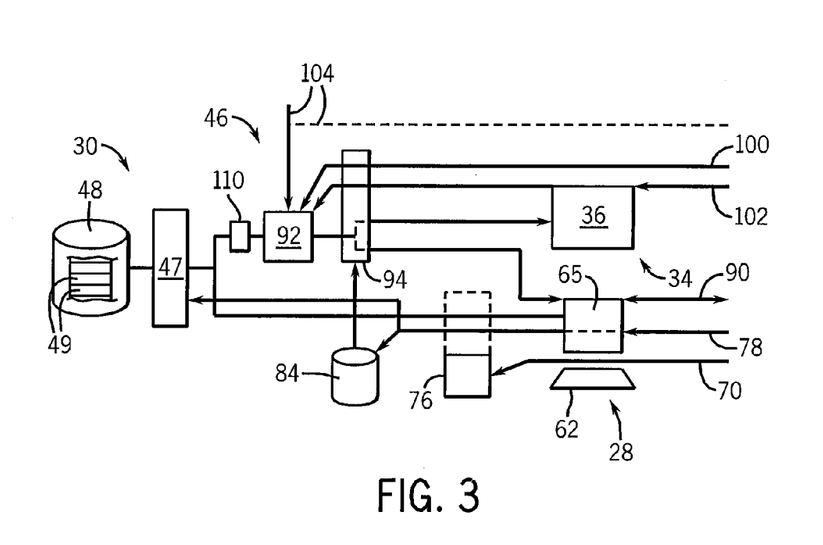
FIG. 3 is a data flow diagram showing communication between the principal components of the present invention according to a stored program implemented by the principal components.
Figure 4:
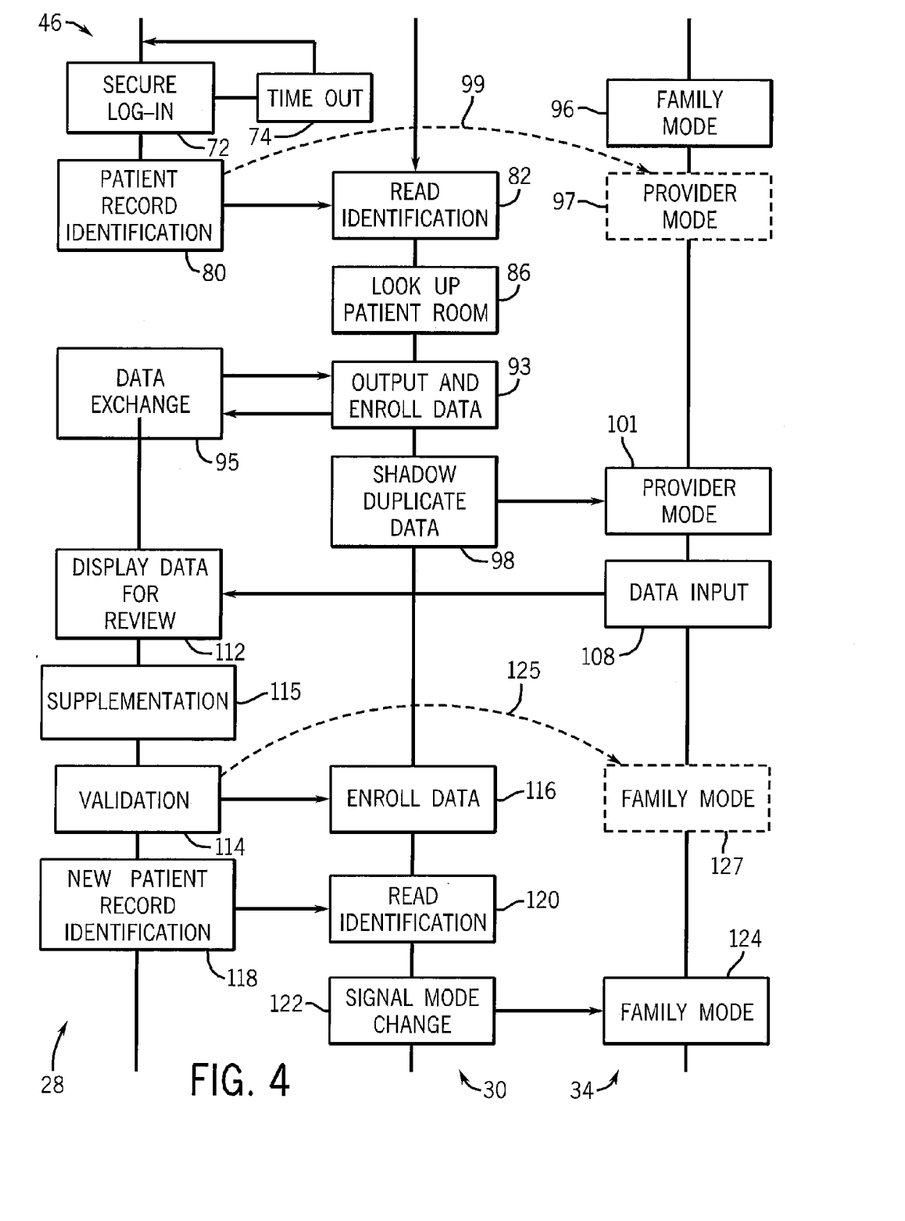
FIG. 4 is a flow chart showing operation of the stored program of the present invention.

Referring now to FIGS. 3 and 4, the program 46 operating in part on the medical database system 30, the room-based terminal 34, and the patient care computing device 28, establishes a set of data linkages between these components permitting the room-based terminal 34 to augment the tasks of the patient care computing device 28 during a healthcare provider's normal workflow. Generally, the patient care computing device 28 receives security information 70 from the healthcare provider identifying the healthcare provider and the authority of the healthcare provider to access the records 49 of the medical database system 30. Such security information 70 may include an identification of the healthcare provider and password information, for example, manually entered through the keyboard of the patient care computing device 28. Alternatively, this security information may be entered using more advanced authentication techniques such as biometrics to provide a secure log-in as indicated by process block 72 of FIG. 4.

According to an exemplary embodiment, the location of the patient care computing device and/or the location of the user may be utilized in determining identifying the patient whose data is to be displayed during the secure access procedure. For example, an RFID tag associated with the device 28 and/or the user may be used to determine that the device is in a specific patient room. This information may be used to determine the display mode and information that is displayed on the room-based terminal 34 for that patient's room. Advantageously, determining a location ensures that the information is displayed based on the presence of the user of the device 28.

Standard security procedures such as an automatic log-out, indicated by process block 74, may be implemented to reduce the chance that unauthorized access to medical database system 30 is obtained, particularly in situations where the healthcare provider may be moving between the patient 15 in a patient room and a remotely stationed mobile work unit 18.

The security information 70 may be received by authentication module 76, typically implemented in software in the medical database system 30 blocking access to the medical database system 30 for unauthorized individuals.

The healthcare provider, operating the patient care computing device 28, may periodically input patient identification information 78 indicating records 49 stored in the mass storage device 48 of the medical database system 30 that the healthcare provider wishes to access, as indicated by process block 80. This patient identification information 78 may be routed to the medical database program 47 which reads the relevant records 49 from the mass storage device 48 as indicated by process block 82. The patient identification information 78 may also go to a patient-room lookup table 84 providing a mapping between each patient and the particular patient room 10 to which they have been assigned, as indicated by process block 86. This mapping drives a connection to a particular room-based terminal 34 in proximity to that patient.

The identification of the patient by patient identification information 78 may also automatically change the mode of the room-based terminal 34 as indicated by process block 97 of FIG. 4 as indicated by dotted arrow 99 to a provider mode as will be described below.

After log-in and the identification of a patient, clinical medical data 90 may be exchanged between the medical database system 30 and the patient, care computing device 28, with data input at the patient care computing device 28 passing to the medical database program 47 to be entered into the records 49 within the mass storage device 48, and data from the mass storage device 48, as processed by the medical database program 47, proceeding through a file format engine 92 and then a router 94 to be returned to the patient care computing device 28.

The router 94 contains information identifying the particular patient care computing device 28 associated with the patient identification information 78 using a work unit assignment table of a type known in the art linking healthcare providers to particular mobile work units 18. This communication is indicated by process block 95 and 93 and follows techniques generally understood in the art.

As indicated by process block 98, data from the medical database program 47 responding to the patient identification 78 provided by the patient care computing device 28 may also be routed by router 94 to the room-based terminal 34 providing an alternative mechanism to change the mode of the room based terminal 34 to the provider mode per process block 101. This routing makes use of the information from the patient-room lookup table 84 and will provide data that generally duplicates some or all of the data provided to the patient care computing device 28 thereby providing the healthcare provider with multiple sources of data about the patient as the healthcare provider moves between the patient care computing device 28 and the patient room 10. The content and format of this data may be determined by the file format engine 92.

The display mode of the room based terminal may further be configurable using the patient care computing device 28. For example, where a practitioner is reviewing data on device 28 and wishes to display some or all of the information to others in the room, such as additional practitioners, patient relatives, etc., the practitioner may use device 28 to modify the display mode and display only the information desired on the room-based terminal 34.

The display mode of the room-based terminal 34 may further be configured to change based on programmed mode change factors. Exemplary mode change factors may include time of day, ambient light, occurrence of a clinical scenario based on changes in information received from one or more monitoring devices, a patient's condition, for example indicating a patient needing specific care routines, etc.

Typically, before the room-based terminal 34 is changed to the provider mode per process blocks 97 or 101, the room-based terminal 34 may operate in a different mode to provide alternative functions that provide an option to idling the display, for example, by blanking its screen. This mode switching helps prevent sensitive information from being displayed publicly through the room-based terminal 34 without the control normally enforced by the healthcare provider. According to an exemplary embodiment, the data to be displayed in any mode may be customizable by the user of the patient care computing device 28. Further, the data displayed on terminal 34 may be different from the data displayed on the device 28 such that, for example, a doctor may still view their desired information while a registered nurse is using the device 28. In one example, the different mode may be a family mode indicated by process block 96 as will be described further below.

Referring still to FIGS. 3 and 4, room-based terminal 34 may operate as a touch screen to provide for touch data 100, for example, indicating an x-y-coordinate of a touch on the display area 36. This touch data 100 may be interpreted by the file format engine 92 according to the formatting of the various elements on the display area 36 and generally will provide commands or data entry that is context sensitive to the particular data on the display area 36 as will be described below.

Medical data input at the room-based terminal 34, as indicated by process block 108, may be received in a buffer 110 implemented by the medical database program 47 before enrollment of the data in the records 49 of mass storage device 48. While stored in the buffer 110, the medical data is not accessible to other users of the medical database system 30. As shown in FIG. 4, this buffered data may be presented at the patient care computing device 28 as indicated by process block 112 for validation, revision, or supplementation, accommodating the reduced security of data possible at the room-based terminal 34 and its decreased data entry capabilities.

At the patient care computing device 28, the data entered from the room-based terminal 34 may be simply validated as indicated by process block 114 or may be supplemented as indicated by process block 115 using a standard text editor or the like. This two-step process of data entry at the room-based terminal 34 then validation at the patient care computing device 28 allows the healthcare provider to enter data at the bedside that provide accurate reminders when the healthcare provider returns to the patient care computing device 28. The patient care computing device 28 may be programmed to remind the healthcare provider of the need for validation/supplementation either through a special window appearing on the display of the patient care computing device 28 or an occasional pop-up reminder.

Once the data is validated as indicated by process block 114 it may be enrolled in the database as indicated by process block 116. This validation process may automatically change the mode of the room-based terminal 34 to the family mode as indicated by process block 127 of FIG. 4 as indicated by dotted arrow 125.

The room-based terminal 34 may also output viewer information 102 relevant to imputed viewers of the display area 36. This viewer information 102, as provided to the file format engine 92, can be used to change the display mode and the data displayed as will be described below and may make use of the data collected from the proximity sensor 54 in FIG. 2 discussed above. Finally, the room-based terminal 34 or an external source may provide screen mode data 104 (for example, from a photocell or manually activated switch) indicating whether the display area 36 should be in a bright or dim format. The latter is intended to permit patient rest without unintended interference from the bright light of a large format room-based terminal 34 while still providing useful data to healthcare providers having night rounds.

As indicated by process block 118, after the healthcare provider completes the duties associated with the current patient, he or she may return to the patient care computing device 28 and enter the patient identification information 78 for a new patient. This new patient identification information 78 will be read at the medical database system 30 as indicated by process block 120. Upon patient change, as an alternative to process block 127, the program 46 may provide a mode change signal as indicated by process block 122 converting the room-based terminal 34 back into family mode as indicated by process block 124. Alternatively or in addition, the room-based terminal 34 may automatically switch out of the provider mode based on a defined parameter, such as after a period of time, or may go to a blanking mode to prevent exposure of sensitive information.

In these diagrams, the operation of the program has been separated into columns roughly corresponding to the different principle components of the present invention; however, it will be understood that the program may be flexibly distributed among these interconnected elements and this depiction only represents one embodiment of the invention.

Figure 5:
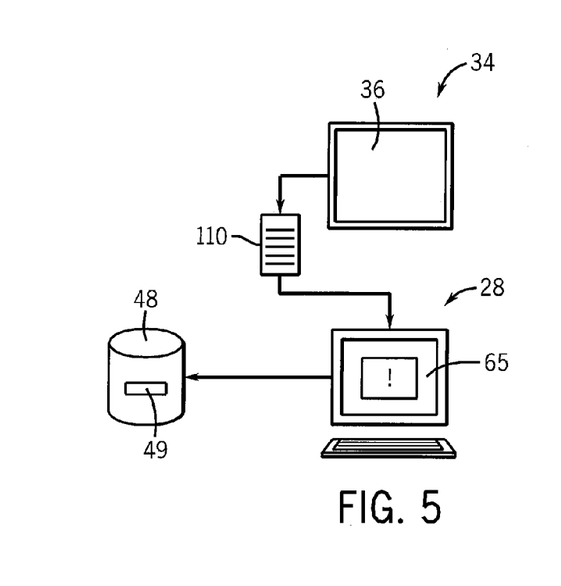
FIG. 5 is a data flow diagram similar to FIG. 3 showing data flow occurring after data entry at the room-based terminal.

Referring now to FIG. 5, the present invention can greatly simplify the entry of contemporaneous data into the patient's record 49 from the room-based terminal 34 without the need for the room-based terminal 34 to have a full set of data entry hardware such as a keyboard and mouse or the overhead of a high level of validation and security for such data entry. This is accomplished by enlisting the strengths of both the room-based terminal 34 and patient care computing device 28 in which the room-based terminal 34 permits simplified, partial, qualitative, and/or quantitative data to be entered, for example through a touch screen interface, and stored in buffer 110 for review at the patient care computing device 28 before being enrolled in the record 49 for the patient. When the healthcare provider is next at the patient care computing device 28, a reminder is provided on the workstation display 65 and the data from the room-based terminal 34 may be reviewed, corrected, edited, supplemented and/or validated, the former four by conventional editing tools known to those of ordinary skill in the art and the last by simply invoking a validation button or the like to indicate validation by the authorized user of the patient care computing device 28.

Prior to validation, the data may be stored and accessible to users of a patient care computing device 28 provided the user has been allowed access through a security or workflow protocol. This temporary storage allows validated workers to review and provide comments on the stored information prior to its storage in the medical records. Upon validation, the data is enrolled in the record 49 for the current patient, meaning it can be accessed by other users of the medical database system 30. The validated and enrolled data may be forwarded as part of the data sent to the room-based terminal 34 the next time the room-based terminal 34 is in the provider mode.

Although described as using a touch screen interface, room-based terminal may additionally include hardware and software allowing use of one or more external input devices. Exemplary input device may include a wireless keyboard and/or mouse, a wired keyboard, a handheld scanner, an audio input device, a still and/or video camera, etc.

Figure 6:
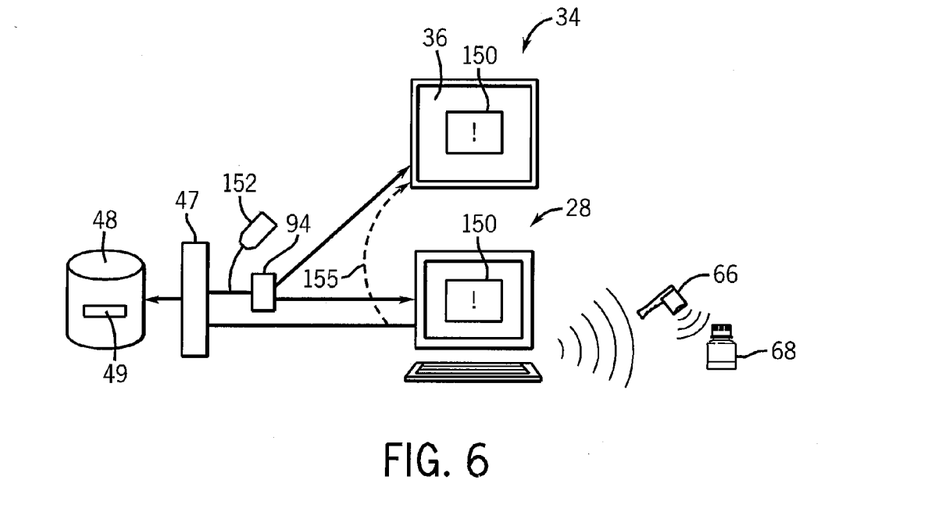
FIG. 6 is a data flow diagram similar to FIG. 4 showing data flow during data entry through the patient care computing device from a remote location.

Referring now to FIG. 6, patient care computing device 28 may include, for example, a remotely usable reader 66 used for scanning medicines 68. In one useful application of the present invention, the reader 66 may be carried with the healthcare provider away from the patient care computing device 28 to be used at the patient's bedside with the patient care computing device 28 positioned remotely, for example in the hallway 20, as shown in FIG. 1. The process of scanning the medicines 68, for example, may result in one or more notifications 150 being generated at the patient care computing device 28, for example, indicating the wrong medicines are being administered or delivered at the wrong time, or providing changes in medication instructions with respect to the medicines 68. Because the reader 66 allows flexibility in the location of the healthcare provider, for example at the patient's bedside, during the administration of the medication, these notifications 150 might not be visible to the healthcare provider contemporaneously with the administration of the medicine. The present invention therefore allows this these notifications 150 or updates to be broadcast both to the patient care computing device 28 and the room-based terminal 34.

Specifically, in this example, the reader 66 provides data to the patient care computing device 28 which may provide that data to the medical database program 47. The medical database program 47 may then generate an advisory message. In one embodiment, the advisory message may be tagged with a high priority network header 152 to be transmitted in high priority to room-based terminal 34 to provide the necessary bedside advisory to the healthcare provider at the time of medicine administration. Alternatively, it is possible for the patient care computing device 28 to provide a direct connection path 155 to the room-based terminal 34 to bypass any network delays.

According to another exemplary embodiment, the medical database system 30, the patient care computing device 29, and the room-based terminal 34 may be configured to monitor recorded data to prevent the display of stale data for some or all of their associated data. For example, where terminal 34 is configured with an update cycle of 30 seconds and data is changed at the patient care computing device, the data displayed on the terminal 34 may be stale data for the remaining 25 seconds of the refresh cycle. Accordingly, for some or all of their data, the components may be configured to force updates on one or more other components based on a detected change in the data.

This same benefit may be provided to other types of data acquisition, for example collecting information from bedside equipment, where the healthcare provider should be provided with immediate feedback.

Figure 7:
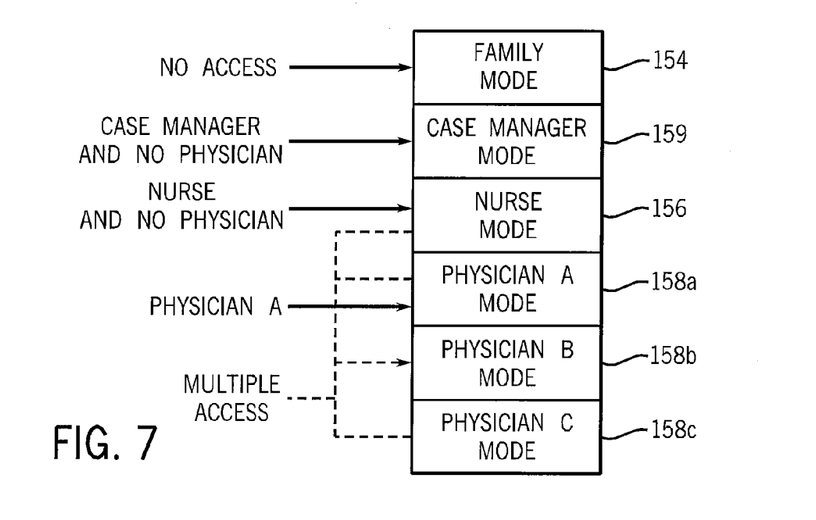
FIG. 7 is a mode-state diagram as may be implemented by the present invention to provide for multiple use of the room-based display for different imputed observers.
Figure 8:
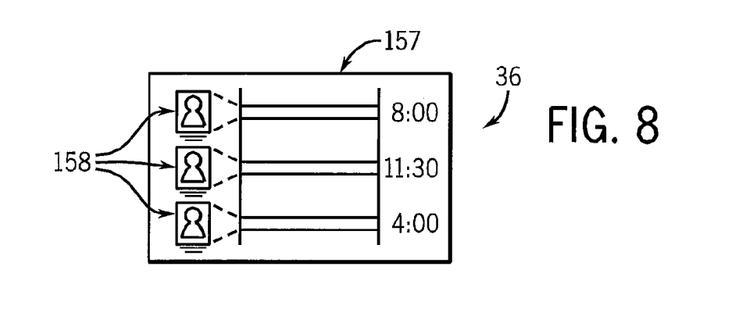
FIG. 8 is a simplified representation of the room-based display when used in the family mode of FIG. 7.

Referring now to FIG. 7, the economic practicality of room-based terminal 34 may be increased by freeing the room-based terminal 34 for other purposes when it is not being used to provide bedside data entry and reporting by the healthcare provider. Generally, the present application anticipates that the room-based terminal 34 may operate in a variety of modes controlled by the file format engine 92 including, for example, a family mode 154, a case manager mode 159, a nurse mode 156 (providing information traditionally useful for a nurse, but not necessarily limited to use by nurses), and multiple physician modes 158*a-c* usable for particular specialists. Generally, the family mode may include conventional use of the display, for example, for entertainment such as playing movies, television or the like. Alternatively, as shown in FIG. 8, the family display may provide a rounds schedule 157, shown here in the form of a day-planner display, indicating the patient's scheduled appointments with doctors, together with names of the doctors and their pictures 158, to keep family members up-to-date about the healthcare of the patient.

The various physician modes 158*a-c* may provide displays useful for physicians formatted according to their particular specialties.

Referring again to FIG. 7, switching between the modes may be accomplished as described above with respect to FIG. 4, in which switching between the family mode and the nurse mode occurs based on whether a healthcare provider is accessing the patient records for the patient associated with the particular room-based terminal 34. Thus, family mode may be used when there is no access by the healthcare provider. Access by the nurse without a physician present will normally cause a switching to the nurse mode. Finally, access by a physician may override other accesses to switch the display to the format for the particular physician's specialty.

In one embodiment, presence of the physician or nurse may be detected, for example, by a real time location system (RTLS) such as RFID tags worn by the nurses and/or physicians. A hierarchy rule may be established in the program 46 to manage the event in which multiple RFID tags for different physicians are in proximity to the room-based terminal 34. For example, an emergency responder might be given higher priority than an internist according to the policies of the hospital. The room-based terminal 34 may also adopt a mode for a composite viewer when there are multiple viewers in the area, the composite mode providing a compromise or universal set of data.

The particular mode selected by program rules may be overridden, for example, by touch buttons on the display.

Figure 9:
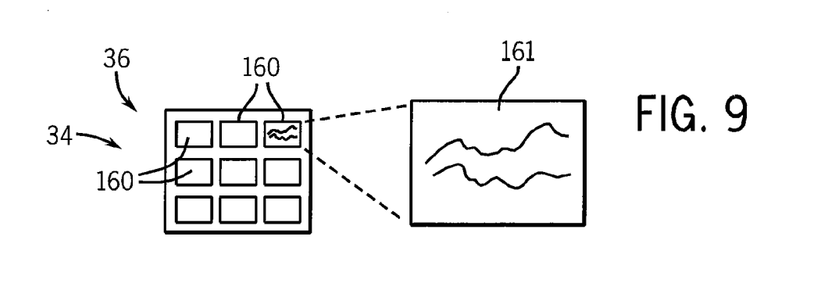
FIG. 9 is a simplified diagram of display modules available during use by the room-based terminal for augmenting the data display of the patient care computing device by expansion of display modules from an overview mode into a detailed mode.

Referring now to FIG. 9, this room-based terminal 34 may be substantially larger than that available on the patient care computing device 28 shown in FIG. 1. Accordingly, a substantially wider range of information may be presented simultaneously on the room-based terminal 34. The present invention contemplates that the display area 36 will be occupied by display modules 160, for example, which can be separately authored according to a standard software development kit (SDK) that provide for a display front end for data from the medical database system 30. Each of the display modules 160 dynamically displays particular types of data to provide a quick overview of top-level data for the patient. Referring to FIG. 9 and FIG. 3, tapping on the display area 36 of the room-based terminal 34 in the area of a display module 160 transmits the touch screen coordinates 100 to the format engine 92. There, it may be mapped to particular display modules 160 to invoke an enlarged view 161 of that display module 160 expanding the portion of display area 36 used and providing greater detail to the information. The code for each display module 160 provides instructions for both of these display sizes.

Figure 10:
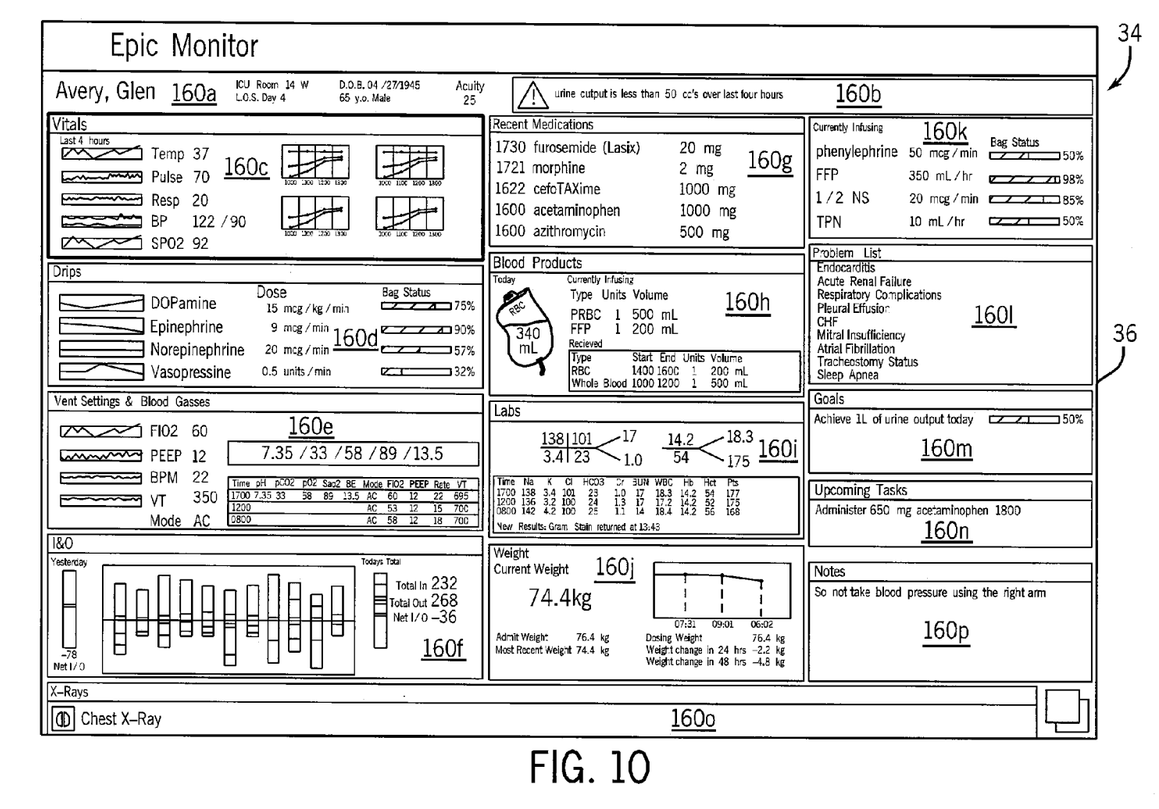
FIG. 10 is a detailed representation of the overview mode of FIG. 9.

Referring now to FIG. 10, an example of the display area 36 of a room-based terminal 34 is shown having multiple display modules 160 arranged in rows and columns including: patient identification information display modules 160*a*, advisories display modules 160*b*, vitals display modules 160*c*, drips display modules 160*d*, vent settings and blood gases display modules 160*e*, I&O display modules 160*f*, recent medications display modules 160*g*, blood products display modules 160*h*, labs display modules 160*i*, weight display modules 160*j*, infusions display modules 160*k*, problem list display modules 160*l*, goals display modules 160*m*, upcoming tasks display modules 160*n*, x-rays display modules 160*o*, and notes display modules 160*p*. This example demonstrates the large amount of information that can readily be handled on large-area monitors suitable for the room-based terminal 34.

Generally, the patient identification information display modules 160*a* provide the patient name, information about his or her room to verify the patient-room lookup table 84, date of birth, age, and other basic biographical information. The advisory display modules 160*b* provide any notifications, for example the medical notifications 150 described above for the patient. The vitals display modules 160*c* provide basic patient chart information of temperature, pulse, respiration, blood-pressure, and specific oxygen, as well as trending graphs showing the results of specific treatment. The drips display modules 160*d* show the current status of IV drips and may be linked to automatic instrumentation as is understood in the art. Similarly, the vent settings and blood gases display modules 160*e* provide data for these settings and gases. I&O display modules 160*f* provide a trend bar chart for fluid intake and output, while recent medications display modules 160*g* provide a list of medications as verified by barcode scanning or the like and contained in the medical database system 30. Blood products display modules 160*g* provide information about the blood products given to the patient as may be also subject to bar scanning. Labs display modules 160*i* similarly provide the result of recent lab tests. Weight display modules 160*j* show a time graph of the patient's weight plus other information such as their admission weight and net weight changes, while infusions display modules 160*k* provide at-a- glance information about the status of infusion bags. The problem list display modules 160*l* provide a place for recording clinically observed problems that the patient is having for quick reference by other physicians. Goals display modules 160*m*, upcoming tasks display modules 160*n*, and notes display modules 160*p* provide free text areas for the physicians to post notes to communicate with other physicians and the nurse. The x-rays display modules 160*o* may provide access to large scale renderings of actual x-rays or images from other imaging modalities such as CT, PET and MRI in the manner of an electronic light box.

Figure 11:
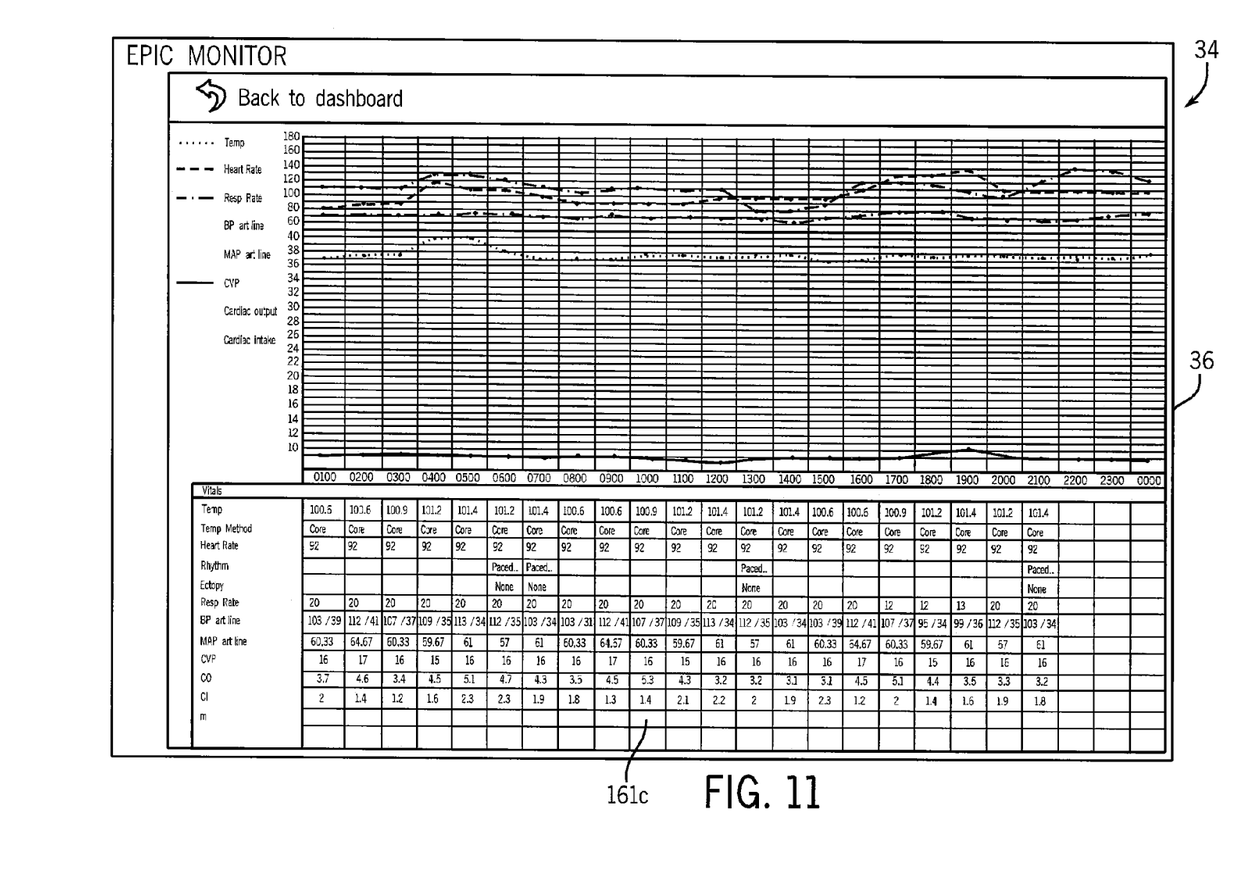
FIG. 11 is a detailed representation of the detail mode of FIG. 9.

Referring now to FIG. 11, as noted above, tapping on display modules 160*c*, in the manner described above, provides an enlarged view 161*c* of the data of the display module 160*c* presenting more detailed information, in this case, time series graphs of all vitals together with a quantitative table of this and additional information. In this way, the benefits of a quick overview of medical data and detailed information can be provided and the large form factor of the display area 36 may be utilized to provide a significantly greater amount of simultaneous data without loss of intelligibility.

Figure 12:
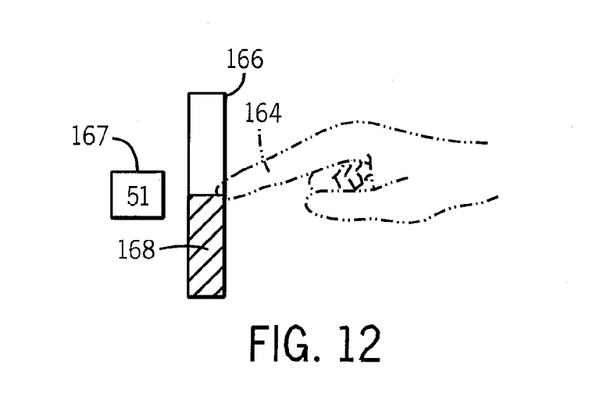
FIG. 12 is a fragmentary view of the display of the room-based terminal showing a display control allowing a sliding entry of quantitative data.

Referring now to FIG. 12, although the room-based terminal 34 may be fitted with a keyboard or in fact may employ a virtual keyboard implemented through the touch screen, rapid quantitative data entry may be obtained through display modules providing for the detection of a sliding movement of a stylus 164 such as the healthcare provider's finger within a target zone 166 while outputting a quantitative number 167 changing continuously according to the position of the stylus 164 within the target zone 166. That position may be highlighted with a shaded bar 168. Using this technique, quantitative information whose significance is derived from the context of the particular display modules can be input.

Figure 13:
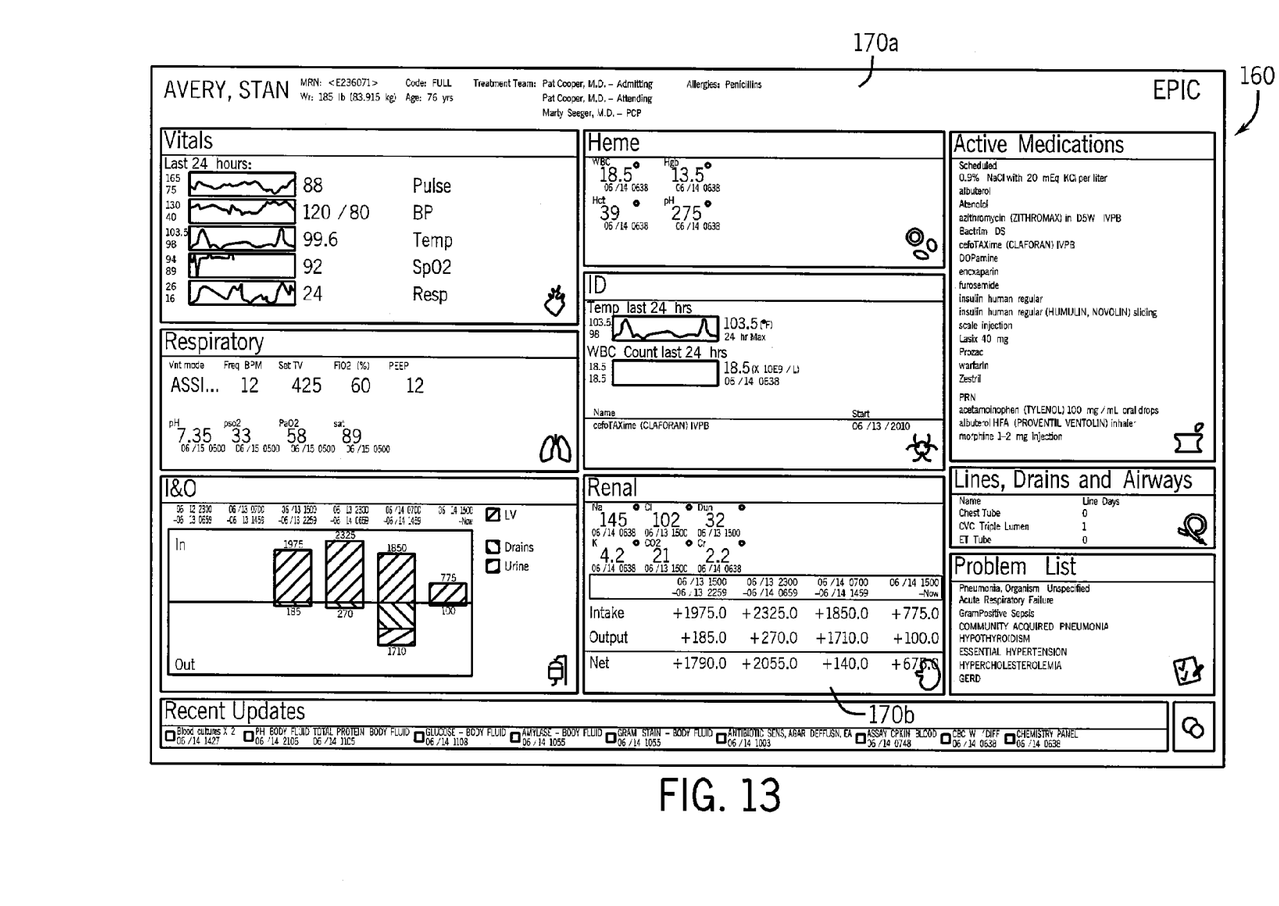
FIGS. 13 and 14 are representations of display modules in day and night modes.
Figure 14:
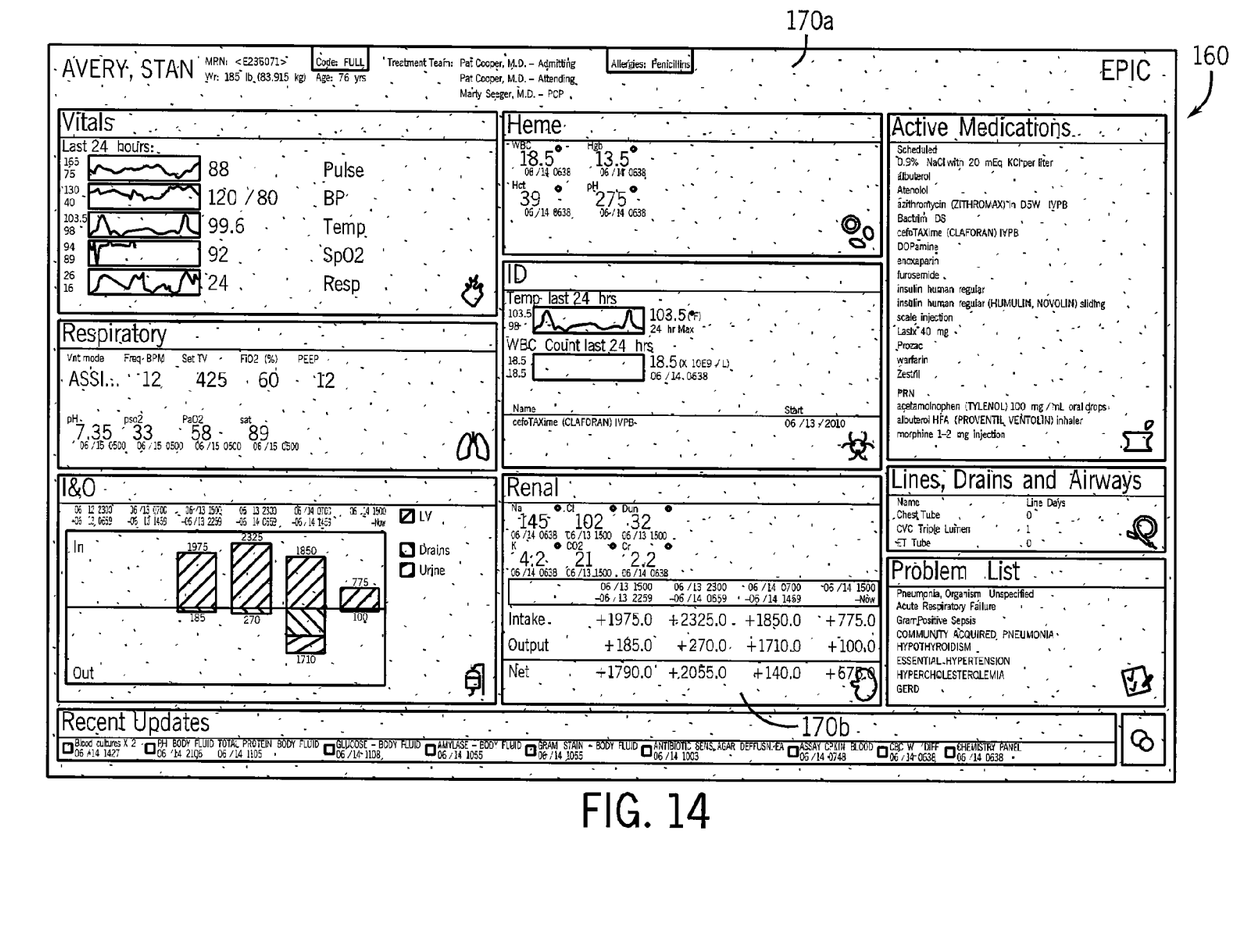

Referring now to FIGS. 13 and 14, generally each display module 160 will be composed of many pixels defining areas 170, for example a background area 170*a* and a data area 170*b*. The considerable light output of the room-based terminal 34 may interfere with the patient's rest and, accordingly, each display module 160 may be operated in both a daylight mode shown in FIG. 13 and a night mode shown in FIG. 14 in which the night mode reduces the total light output from the display area 36 by reducing the product of the number of pixels and brightness of each pixel over the entire display module. This may be done, for example, without reducing contrast or dimming the entire display, by adopting dark backgrounds, using negative images, or other adjustments to graphic features which may be determined on a display module by display module basis. The particular mode (daylight or night) may be switched by detection of light in the patient room 10, manually, or according to a schedule managed from a central location. Importantly, unlike a screen blanking operation, the night mode continues to provide a display of critical data about the patient while reducing total light output.

Figure 15:
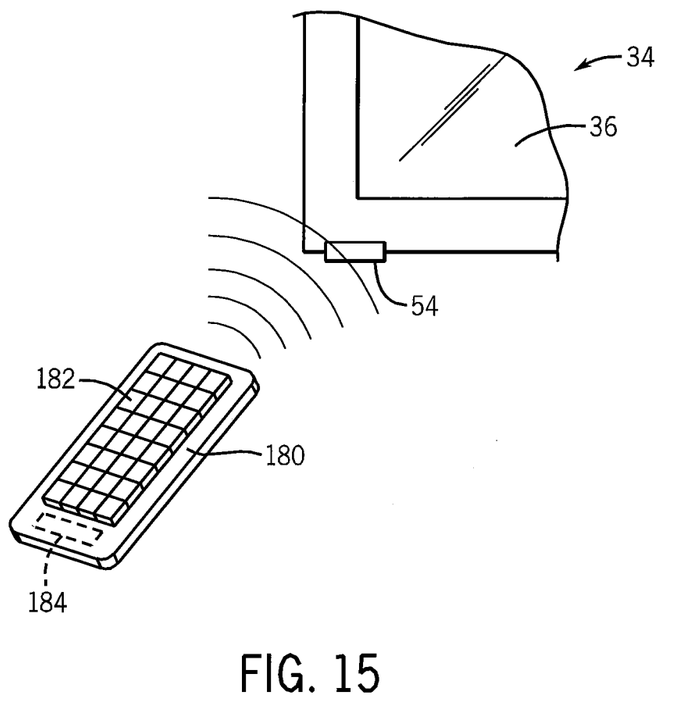
FIG. 15 is a fragmentary perspective view of the room-based terminal of FIG. 2 showing proximity sensing of a handheld device for display mode changes and data entry.

Referring now to FIGS. 2 and 15, the proximity sensor 54 may in an alternative embodiment be a wireless transceiver, for example, one that may communicate with a handheld electronic device 180 such as a cell phone, PDA or the like. The proximity sensor 54 in this case may use a service discovery protocol, for example, Zeroconf, or its implementation of Bonjour by Apple Computer, to detect the presence of the portable handheld electronic device 180. Discovery of the portable handheld electronic device 180 may be used to trigger a change in the mode of display 34 automatically or by command from the user of the portable handheld device 180 using the portable handheld device 180. In the former case, the handheld electronic device 180 may run an application program 184 identifying the user with respect to the modes discussed above with respect to FIG. 7. This embodiment of the invention can be useful when portable electronic devices 180 are used by a healthcare professional for additional purposes such as for timely data capture during rounds.

The application program 184 may further permit a splitting of functions of data entry with the user interface of the handheld electronic device 180, for example, its touch display 182 or keyboard, used as an in-room data entry device, while using the display 34 for the display of the data being entered. In this case, the application program 184 may also provide for the entry modes discussed with respect to FIG. 12 and receive data from the medical database system 30 via the proximity sensor 54 to provide the information for data entry.

The present invention has been described in terms of the preferred embodiment, and it is recognized that equivalents, alternatives, and modifications, aside from those expressly stated, are possible and within the scope of the appending claims.

We claim:

1. An electronic medical record system comprising:
   (a) a medical database system providing a communication interface for receiving and transmitting medical data related to patients;
   (b) a patient care computing device including an electronic display, a text entry device, and a network circuit communicating with the medical database system;
   (c) at least one stationary, room-based terminal providing:
      (i) an electronic display adapted for mounting relative to a bedside associated with a given patient;
      (ii) a network circuit communicating with the medical database system; and
   (d) a communication network communicating the with the network circuits of the medical database system, the patient care computing device, and the room-based terminal,
   wherein the medical database system, patient care computing device, and room-based terminal execute at least one stored program to:
      (i) manage a secure log-on by a health care worker to the patient care computing device;
      (ii) receive through the patient care computing device after log-on, an identification of a patient;
      (iii) communicate patient medical data related to the patient from the medical database system to the patient care computing device through the communication network;
      (iv) display the patient medical data on patient care computing device;
      (v) receive a selection, at the patient care computing device of a portion of the patient medical data that is a subset of the displayed patient medical data;
      (vi) transmit the selection of the portion of the patient medical data to the medical database system through the communication network;
      (vii) provide duplicate communication of the portion of the patient medical data from the medical database system to the room-based terminal associated with a bedside of the patient through the communication network; and
      (viii) receive a modification of the portion of the patient medical data communicated to the room-based terminal over the communication network and transmit the modified portion over the communication network to the patient care computing device for validation prior to acceptance of the data into the medical database system.

2. The electronic, medical record system of claim 1 including a plurality of room-based terminals wherein the stored program includes a patient room table, the patient room table mapping the patient to an address of the room-based terminal associated with a bedside of the patient; wherein the medical database system further includes a means for directing the duplicate communication according to the address.

3. The electronic medical record system of claim 2 wherein the room-based terminal is a touch screen.

4. The electronic medical record system of claim 3 wherein the room-based terminal provides graphical elements for quantitative data entry employing a detection of a sliding of a stylus on the touch screen.

5. The electronic medical record system of claim 3 wherein the room-based terminal provides a plurality of display icons that may be touched to expand them to larger icons.

6. The electronic medical record system of claim 1 wherein the room-based terminal and patient care computing device provide for input of medical data and wherein the stored program further:

(v) communicates medical data from the room-based terminal and patient care computing device to the medical database records related to the patient.

7. The electronic medical record system of claim 6 wherein the stored program is configured to force an update for at least some medical data input at the patient care computing device to be communicated to the room-based terminal.

8. The electronic medical record system of claim 7 further including a device for recording an administering of medicine, the device in communication with the patient care computing device, wherein the stored program provides an advisors based on recordation of medicine administering at both the patient care computing device and the room-based terminal.

9. The electronic medical record system of claim 6 wherein the stored program further operates to display supplementary information on the room-based terminal related to generic roles of imputed observers selected from at least two of the group consisting of: a physician imputed user, a family member imputed user, a case manager imputed user, and a nurse imputed user.

10. The electronic medical record system of claim 1 wherein the medical record system receives data identifying an imputed observer of the room-based terminal and wherein duplicate communication is selectively displayed according to the identification of the imputed observer.

11. The electronic medical record system of claim 10 wherein the identification of an imputed observer is performed by a presence-sensing of at least one person in proximity of the room-based terminal.

12. The electronic medical record system of claim 11 wherein the stored program provides a set of priority rules identifying one imputed observer when there are multiple persons sensed in proximity of the room-based terminal.

13. The electronic medical record system of claim 10 wherein the identification of an imputed observer is performed by detecting the health care worker logged into the patient care computing device.

14. The electronic medical record system of claim 1 wherein a display mode of the room-based terminal is based on a clinical condition of the patient.

15. The electronic medical record system of claim 1 wherein a display mode of the room-based terminal displays a selection of patient information from a patient care computing device when the patient care computing device is being used to access patient information and the patient is associated with the room-based terminal.

16. The electronic medical record system of claim 1 wherein the patient care computing device is associated with a mobile cart providing carrier surfaces for medical supplies and for the patient care computing device.

17. A computer implemented method for providing patient medical information at a room-based terminal in communication with a patient care computing device, comprising:

(a) receiving an access request from the patient care computing device in proximity to a patient room at a medical database processor of a computer-implemented medical database system using a secure access process over a communication network;

(b) identifying the room-based terminal using the medical database processor based on a detected location of the patient care computing device in proximity to the patient room based on information stored in the medical database system; and (c) communicating patient medical data related to a patient associated with the detected location from the medical database system over the communication network to the patient care computing device, receiving a selection of a portion of the patient medical data over the communication network that is a subset of the patient medical data; and communicating the selected portion of the patient medical data over the communication network to the room-based terminal associated with the detected location; and (d) receiving a modification of the portion of the patient medical data communicated to the room-based terminal at the medical database processor over the communication network and transmitting the modified portion over the communication network to the patient care computing device for validation prior to acceptance of the data into the medical database system.

18. A computer implemented method for providing patient medical information at a room-based terminal in communication with a patient care computing device, comprising:

(a) receiving an access request from the patient care computing device using a secure access process at a medical database processor of a computer-implemented medical database system over a communication network, the access request identifying a patient;

(b) identifying the room-based terminal using the medical database processor based on the patient identification based on information stored in the medical database system;

(c) communicating patient medical data related to a patient associated with the detected location from the medical database system over the communication network to the patient care computing device, receiving a selection of a portion of the patient medical data over the communication network that is a subset of the patient medical data; and communicating the selected portion of the patient medical data over the communication network to the room-based terminal associated with the detected location; and (d) receiving a modification of the portion of the patient medical data communicated to the room-based terminal at the medical database processor over the communication network and transmitting the modified portion over the communication network to the patient care computing device for validation prior to acceptance of the data into the medical database system.

19. The computer implemented method of claim 18, further including receiving a input indicating the an administration of medicine at the patient care computing device and providing an advisory based on recordation of medicine administering at both the patient care computing device and the room-based terminal.

\* \* \* \* \*